(12) United States Patent
Chen et al.

(10) Patent No.: US 11,337,680 B2
(45) Date of Patent: May 24, 2022

(54) INTEGRATED DEVICE FOR FAECES SAMPLING AND OCCULT BLOOD DETECTION

(71) Applicant: Hangzhou New Horizon Health Technology Co. Ltd., Hangzhou (CN)

(72) Inventors: Yiyou Chen, San Jose, CA (US); Bin Li, Hangzhou (CN); Shuidi Zhong, Hangzhou (CN)

(73) Assignee: Hangzhou New Horizon Health Technology Co. Ltd., Hangzhou (CN)

( * ) Notice: Subject to any disclaimer, the term of this patent is extended or adjusted under 35 U.S.C. 154(b) by 253 days.

(21) Appl. No.: 16/484,731

(22) PCT Filed: Sep. 21, 2017

(86) PCT No.: PCT/CN2017/102799
§ 371 (c)(1),
(2) Date: Nov. 21, 2019

(87) PCT Pub. No.: WO2018/149131
PCT Pub. Date: Aug. 23, 2018

(65) Prior Publication Data
US 2020/0205788 A1    Jul. 2, 2020

(30) Foreign Application Priority Data

Feb. 14, 2017 (CN) .......................... 201710078782.4

(51) Int. Cl.
*G01N 33/72* (2006.01)
*G01N 33/49* (2006.01)
(Continued)

(52) U.S. Cl.
CPC ......... *A61B 10/0038* (2013.01); *G01N 33/72* (2013.01); *G01N 1/02* (2013.01); *G01N 33/49* (2013.01)

(58) Field of Classification Search
CPC ........ A61B 10/0038; A61B 2010/0006; A61B 2010/0216; G01N 1/02; G01N 33/53; G01N 33/72; G01N 33/49
(Continued)

(56) References Cited

U.S. PATENT DOCUMENTS 5,514,341 A * 5/1996 Urata ................. A61B 10/0038
422/534
5,882,942 A * 3/1999 Kagaya .............. A61B 10/0038
436/174

(Continued)

FOREIGN PATENT DOCUMENTS

| CN | 100538326 C | 9/2009 |
|---|---|---|
| CN | 102798542 A | 11/2012 |

(Continued)

OTHER PUBLICATIONS

Extended European Search Report dated Nov. 11, 2020, for EP application No. 17 896 392.2, filed on Sep. 21, 2017, 8 pages.
(Continued)

*Primary Examiner* — Maureen Wallenhorst
(74) *Attorney, Agent, or Firm* — Cooley LLP

(57) ABSTRACT

Disclosed is an integrated device for faeces sampling and occult blood detection, which has functions of quantitative collection, dissolution, filtration, detection with immune test strips of the faecal sample, and is convenient to carry and operate, and the device does not leak any liquid during storage, transportation and detection. The device can accurately collect a constant sample with no pollution and leakage, and can quickly determine results of occult blood without the aid of other items. The device can detect faecal occult blood at any time and at any place, can help to overcome the problem of low rate of inspection due to the inconvenience of faeces submission and inspection, further promote the detection of faecal occult blood, and can (Continued)

improve the early diagnosis and screening rate of colorectal cancer of the population.

7 Claims, 3 Drawing Sheets

(51) Int. Cl.
    *G01N 1/02*     (2006.01)
    *A61B 10/00*     (2006.01)

(58) Field of Classification Search
    USPC ....... 422/400, 401, 402, 405, 408, 409, 412,
                 422/418, 420; 436/63, 66, 164, 165, 169
    See application file for complete search history.

(56) References Cited

U.S. PATENT DOCUMENTS

| | | | |
|---|---|---|---|
| 6,248,294 | B1 | 6/2001 | Nason |
| 10,772,610 | B2* | 9/2020 | Dai .................... A61B 10/0038 |
| 2006/0188939 | A1 | 8/2006 | Gao |
| 2006/0210448 | A1* | 9/2006 | Wang ...................... B01L 3/502 |
| | | | 422/400 |
| 2006/0292034 | A1 | 12/2006 | Gould et al. |
| 2007/0275475 | A1* | 11/2007 | Liang ...................... B01L 3/502 |
| | | | 436/165 |
| 2011/0060137 | A1* | 3/2011 | Tanigami ............. C12Q 1/6806 |
| | | | 536/23.1 |
| 2011/0146420 | A1* | 6/2011 | Okada ................... B01L 3/5021 |
| | | | 73/864.51 |
| 2016/0051235 | A1* | 2/2016 | Wan ................... A61B 10/0038 |
| | | | 436/164 |

FOREIGN PATENT DOCUMENTS

| | | | |
|---|---|---|---|
| CN | 103217313 | A | 7/2013 |
| CN | 106680477 | A | 5/2017 |
| CN | 106769161 | * | 5/2017 |
| CN | 206523509 | U | 9/2017 |
| CN | 207074121 | * | 3/2018 |
| JP | 2007-511769 | A | 5/2007 |
| JP | 2009-524063 | A | 6/2009 |
| WO | WO-2013/141103 | A1 | 9/2013 |
| WO | WO-2016/188362 | A1 | 12/2016 |

OTHER PUBLICATIONS

International Search Report dated Dec. 27, 2017, for PCT application No. PCT/CN2017/102799, filed on Sep. 21, 2017, 3 pages.
Written Opinion of the International Searching Authority dated Dec. 27, 2017, for PCT application No. PCT/CN2017/102799, filed on Sep. 21, 2017, 6 pages.

* cited by examiner

INTEGRATED DEVICE FOR FAECES SAMPLING AND OCCULT BLOOD DETECTION

CROSS-REFERENCE TO RELATED APPLICATIONS

This application is a national stage application of International Application No. PCT/CN2017/102799, filed Sep. 21, 2017, which claims the benefit of Chinese Application No. 201710078782.4, filed Feb. 14, 2017, the contents of all of which are herein incorporated by reference in their entireties.

BACKGROUND

Technical Field

The present invention belongs to medical equipment, and relates to an assistant in vitro diagnosis utensil, and in particular, to an integrated device for faeces sampling and occult blood detection.

Related Art

Faeces occult blood detection is one of important technologies for early diagnosis of colorectal cancer and screening of populations, by performing colonoscopy on patients with faeces occult blood being positive, the tumor detection rate may be increased by 4-6 times, and colonoscopy is an optimal method for screening high-risk populations with colorectal tumor. That the colorectal cancer morbidity and mortality rates are obviously reduced by detecting faeces occult blood every year has already been verified by multiple large-scale queue research institutions. Faeces occult blood detection has been recommended as a leading screening technology for colorectal cancer of the populations by multiple authorities including American Cancer Society, colorectal cancer early diagnosis and early treatment projects of the Ministry of Health of China, Chinese Society of Gastroenterology of Chinese Medical Association and the like.

In conventional faeces occult blood detection, an examinee needs to reserve faeces for submission and inspection, and professional staff of a hospital are needed for detection. However, because the requirements for faeces collection and storage and transportation of the sample for submission and inspection are relatively high, a person going to the hospital for physical examination generally neglects submission and inspection of faeces or does not submit because of having no awareness of defecation. Therefore, in actual population screening and physical examination, faeces sampling and submission and inspection rates are relatively low. In a colorectal cancer screening test performed in Xiacheng District in Hangzhou, Xuhui District in Shanghai and Nanggang District in Harbin, the faeces submission and inspection rate of the community residents does not reach 40%. While actually, an operation method of detecting the faeces occult blood with a colloidal gold test strip is very simple, similar to an early pregnancy test strip, and a community resident can detect and judge at home by himself.

However, faeces detection is obviously different from urine detection. Firstly, faeces is easier to pollute than urine, and no one is willing to directly view or contact the faeces. Secondarily, faeces is solid, and may be subjected to immune test strip detection only after being sufficiently dissolved in liquid first. Then, control on the faeces sampling amount is more difficult than urine. Finally, in detection operation, it must ensure that faecal liquid does not leak, or the faecal liquid is not suitable for household or non-specialized home detection. A utensil for self-detection of faeces occult blood is still absent on the market currently, some factories of faeces occult blood reagent adopting an immunogold method design respective faeces sampling utensils, but the faeces sampling utensils do not have a sampling amount control device, and none of them includes a detector, and in all detection, the faecal liquid must be open. Currently, faeces occult blood is performed by being limited in professional medical institutions, and in detection, the professional staff generally put the faeces into a container with a buffer solution first to dissolve, then pour the faeces liquid in the container into a small cup or a small hole, and then insert a liquid-absorbing test strip into the small cup or the small hole for detection. In detection, the faeces liquid is open, the professional staff need to directly view the faeces for many times, in operation, the small cup and the small hole turn over easily and leak liquid, then the professional staff need to operate by wearing gloves, and the detection utensils are dispersed and do not form a complete set, and thus the detection utensils are inconvenient to carry and transport, these disadvantages cause the situation that the current faeces occult blood cannot be independently examined by a non-specialized person.

Faeces occult blood is early earning for abnormity of the alimentary canal, and when the bleeding amount of the alimentary canal is less, no abnormal change may occur to the outer shape of the faeces, and it cannot be recognized by naked eyes. Therefore, faeces occult blood inspection needs to be performed on a patient suspected to have chronic bleeding in the alimentary canal, which has significant meaning on early screening of malignant tumors (such as stomach cancer, colorectal cancer, polyp and adenoma) of the alimentary canal. In conventional immune detection method, i.e. hemoglobin detection method, the patient needs to go to a professional hospital or physical examination organization for inspection by using a sampling tube or a kit. The patient reserves the faeces sample, the medical inspection personnel samples with the sampling tube, mixes quantitative faeces with a stabilizing solution, and drips the mixed solution into a faeces occult blood kit, and according to the colloidal gold immunochromatography principle, the mixed solution is siphoned by a test strip in the kit and spreads, then a color zone appears, and whether the faeces occult blood is negative or positive is judged by comparison of the color of the color zone with a standard color card.

SUMMARY

The present invention aims to provide an integrated device for faeces sampling and occult blood detection, including a lid, a main body container sealed tube, a stop block, a piston, a test strip slot seat, a sealing sheet, a base, and a faeces sampling stick; the lid is provided with an inner ring and a C-shaped outer ring, the diameter of the inner ring is tightly adapted to the inner diameter of a round tube chamber, a smooth tube wall is adopted to tightly fit to the round tube chamber which can be sealed so as to ensure that no matter in the container leaks, the diameter of the C-shaped outer ring is adapted to the outer diameter of the round tube chamber, the C-shaped outer ring is sleeved over the round tube chamber, a clearance between the inner ring and the C-shaped outer ring is adapted to the tube wall of the round tube chamber, the faeces sampling stick is fixed at the center of the inner ring, the free end of the faeces sampling stick is provided with a threaded structure to be used for staining faeces, the faeces sampling stick is tightly adapted to a round hole inside a separation layer 15, the faeces sampling stick not only can scrape redundant faeces on the threaded surface but also can form secondary sealing when passing so as to prevent inverted overflow of faeces liquid, a small hole is provided in the tube wall of the inner ring at the opening of the C-shaped outer ring to be adapted to a bulge of the stop block, and when the bulge is inserted into the small hole, the stop block can be prevented from sliding up and down, so as to play a role of fixing.

The main body container sealed tube is combined by a round tube chamber for storing liquid and a test strip rectangular tube chamber, the top of the rectangular tube chamber is sealed, the the separation layer which has a funnel shape with a round hole in the center is provided in the round tube chamber, and the diameter of the hole is adapted to the diameter of the faeces sampling stick, so that the threaded structure of the faeces sampling stick passes to scrape residual faeces on the threaded surface.

The size and shape of the stop block are adapted to the section of the rectangular tube chamber, the bulge is provided on the inside wall of the stop block and adapted to a small hole of the lid, so as to realize dismounting and fixing of the stop block, and the stop block is located at the top of the rectangular tube chamber, so as to prevent the faeces sampling stick from inserting in advance due to misoperation.

A test strip slot is provided at one side of the test strip slot seat, the test strip slot communicates with the base, so that glass fiber at the bottom of the test strip may contact with the solution, the other side of the test strip slot seat is provided with a piston slot with a hole in the center, piston supports are provided on the upper edge of the piston slot, so that the piston is supported without sliding down before acting, the outer shape of the test strip slot seat is adapted to the main body container sealed tube, the test strip slot is inserted into the rectangular tube chamber, and the piston slot is located in the round tube chamber.

The base is sleeved with the bottom of the test strip slot seat, a solution receiving slot is provided in the base, a groove is located below the test strip slot, a slope is provided between the receiving slot and the groove, a quantitative solution entering the receiving slot via the piston slot is guided to flow into the groove via the slope, so that the glass fiber at the bottom of the test strip just contacts with the solution in the groove, and the mixed solution starts to spread under the siphon action of the glass fiber of the test strip, and then a color zone appears.

The sealing sheet is clung to the back of the piston slot, and the piston is placed on the piston supports, at the moment, no solution exists in the base, and after the piston is pressed down, the piston rod with a sharp end can pierce the sealing sheet, so that the solution enters the receiving slot of the base quantitatively.

The diameter of one end, close to the lid, of the faeces sampling stick is greater than that of the free end, so as to be matched with the round hole inside the separation layer more tightly.

The volume of the piston slot is set according to a quantitative requirement.

A drying agent is put into the rectangular tube chamber, so as to play a role of protecting the humidity-sensitive colloidal gold test strip.

The main body container sealed tube, the test strip slot seat and the base are assembled together, and hermetical welding of the three is achieved by adopting an ultrasonic welding technology.

The using method of the device of the present invention is as follow:

1. The lid 1 is taken down, and faeces is collected with the free end of the faeces sampling stick, so that the faeces stains the threaded part of the faeces sampling stick.

2. The faces sampling stick 8 is inserted back into the round tube chamber 13, and the utensil is shaken, so that the faeces is sufficiently dissolved in the solution.

3. The stop block 3 is dismounted, the lid 1 is pressed to the bottom, at the moment, the faeces sampling stick pushes down the piston 4, so that the sharp end of the piston rod 11 pierces the sealing sheet 6, and the quantitative mixed solution in the piston slot 12 enters the receiving slot 21 of the base 7.

4. The mixed solution is allowed to flow into the groove 22 of the base 7 via the slope, wherein the bottom of the groove 22 just contacts with the glass fiber at the bottom of the test strip, the mixed solution starts to spread under the siphon action of the test strip, and then a color zone appears.

5. After 10 minutes, the color of the quality control line of an observation window of the test strip and the color a detection line strip are checked, and comparison is conducted with a color card, a result is determined.

Principle of the Present Invention:

The lid 1 with the faeces sampling stick is used for faeces sampling, and the tail end of the faeces sampling stick has a thread, so as to perform quantitative sampling. The lid is inserted into the tube body, a the separation layer which has a funnel shape is provided in the tube body to divide the tube body into an upper tube chamber and a lower tube chamber, a hole with proper size is provided inside the separation layer and just allows the faeces sampling stick with thread to pass, so as to play the role of scraping redundant faeces, the faeces sampling stick reaches the lower tube chamber, the lower tube chamber is filled with the stabilizing solution in advance, and the faeces on the thread of the faeces sampling stick is dissolved in the stabilizing solution to form a sample mixed solution. The stop block is assembled on the lid, early spreading of the test strip caused by misoperation is avoided in the sampling and faeces and stabilizing solution shaking and mixing processes, after sampling is completed, the stop block is dismounted, the lid may be pressed down completely, the piston is pushed to move downwards, the piston is mounted in the test strip slot and is downward pushed into a piston slot 12 of a sealed space formed by the round tube chamber at the lower part of the test strip slot seat, the volume of the sealed space is the transferred quantitative volume of the sample mixed solution, pushing downward is continued, the piston rod at the lower part of the piston ruptures the sealing sheet sealing the small round hole at the lower part of the test strip slot, and the sample mixed solution with quantitative volume is pressed to the base by the small hole 18 in the piston slot 12. The base has a round tube chamber receiving slot 21 for receiving the pressed-in sample mixed solution, the receiving slot 21 has a slope for guiding the sample mixed solution into the groove 22 of the base. The bottom of the test strip stuck by the test strip slot contacts with the sample mixed solution in the groove 22, the mixed solution starts to spread under the siphon action of the glass fiber of the test strip, a color zone appears, and then comparison with the color card may be performed, so as to determine the result. A tablet drying agent may be provided at the clearance of the rectangular tube chamber 14 of the test strip, so as to play the role of protecting the humidity-sensitive colloidal gold test strip, the tube body, the test strip slot and the base are assembled together, and hermetical welding of the three is achieved by adopting an ultrasonic welding technology.

The utensil is simple in structure, low in production cost, and convenient in operation, the faecal liquid does not need to be placed in the open, the test can be completed one time after faeces sampling, and the utensil is clean and safe. By implementation of the present invention, an ordinary person can accurately and cleanly complete faeces occult blood test according to brief introduction without any professional training, and determine the detection result; a constant amount of faeces may be accurately collected, without causing any pollution, or causing faeces liquid leakage, and the occult blood result may be rapidly tested without the aid of other items; a common adult can perform faeces occult detection at any time and at any place; and therefore, the present invention can help to overcome the problem of low rate of inspection due to the inconvenience of faeces submission and inspection, further promote the detection of faeces occult blood, and can improve the early diagnosis and screening rate of colorectal cancer of the population.

The present invention overcomes disadvantages of the prior art, and well solves the foregoing problems, and the invented utensil integrates the functions of quantitative collection, dissolution, filtration, detection with immune test strips of the faeces sample, is convenient to carry and operate, the test can be conducted without directly viewing the faeces after sampling, and the device does not leak any liquid during storage, transportation and detection. A common adult can perform feces occult blood self detection at any time and at any place. According to the present invention, the sampling tube and the test strip are combined in one kit, and the liquid storage tube chamber and the test strip tube chamber are sealed and independent relatively. A patient can detect at home, and can complete sampling, detection and determination at home according to instructions. The operation is convenient and quick. The sample preservation freshness and the detection result accuracy are increased.

DETAILED DESCRIPTION

Figure 1:
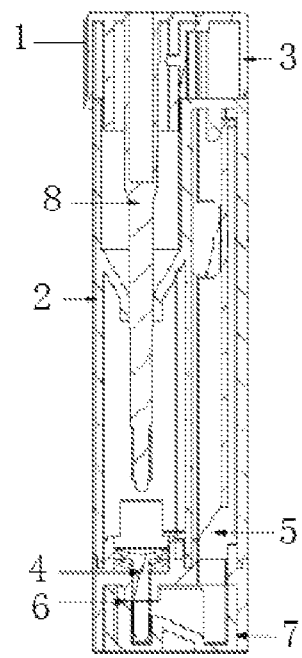
FIG. 1 is a structure schematic diagram of the present invention.
Figure 2:
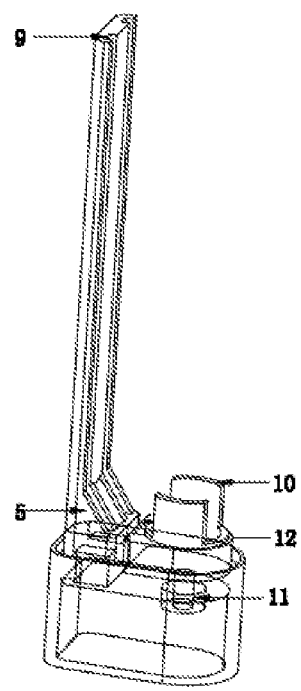
FIG. 2 is a structure schematic diagram of a test strip slot part.
Figure 3:
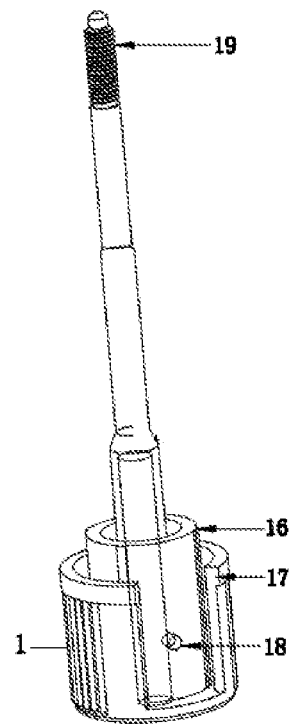
FIG. 3 is a structure schematic diagram of a tube body part.
Figure 4:
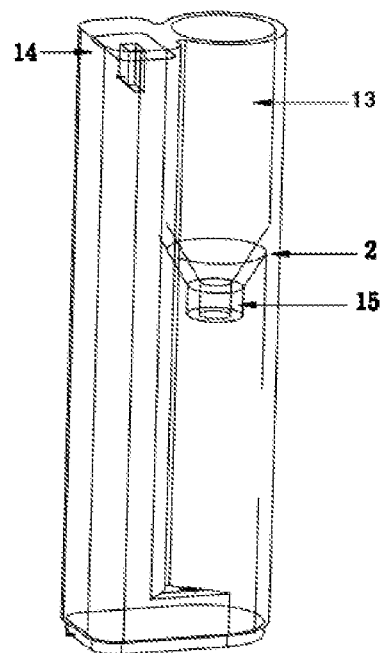
FIG. 4 is a structure schematic diagram of a lid part.
Figure 5:
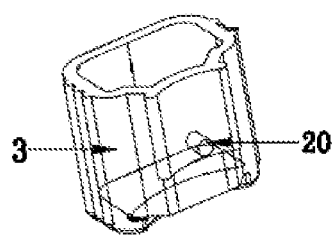
FIG. 5 is a structure schematic diagram of a stop block part.
Figure 6:
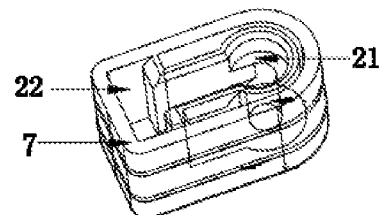
FIG. 6 is a structure schematic diagram of a bottom part.
Figure 7:
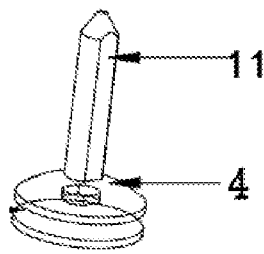
FIG. 7 is a structure schematic diagram of a piston part.

Further description will be made to the present invention in combination with accompanying drawings and embodiments.

Embodiment 1

Referring to FIG. 1 to FIG. 7, the integrated device for faeces sampling and occult blood detection includes a lid 1, a main body container sealed tube 2, a stop block 3, a piston 4, a test strip slot seat 5, a sealing sheet 6, a base 7, and a faeces sampling stick.

The lid 1 is provided with an inner ring 16 and a C-shaped outer ring 17. The diameter of the inner ring 16 is tightly adapted to the inner diameter of a round tube chamber 13. A smooth tube wall is adopted to tightly fit to the round tube chamber 13 which can be sealed so as to ensure that no matter in the container leaks. The diameter of the C-shaped outer ring 17 is adapted to the outer diameter of the round tube chamber 13. The C-shaped outer ring 17 is sleeved over the round tube chamber. A clearance between the inner ring 16 and the C-shaped outer ring 17 is adapted to the tube wall of the round tube chamber 13. The faeces sampling stick 8 is fixed at the center of the inner ring 16. The free end of the faeces sampling stick 8 is provided with a threaded structure 19 to be used for staining faeces. The faeces sampling stick 8 is tightly adapted to a round hole inside a separation layer 15. The faeces sampling stick 8 not only can scrape redundant faeces on the threaded surface but also can form secondary sealing when passing so as to prevent inverted overflow of faeces liquid. The inner ring 16 has a small hole 18 in the tube wall at the opening of the C-shaped outer ring 17 to be adapted to a bulge 20 of the stop block 3. When the bulge 20 is inserted into the small hole 18, the stop block 3 can be prevented from sliding up and down, so as to play a role of fixing.

The main body container sealed tube 2 is combined by a round tube chamber 13 for storing liquid and a test strip rectangular tube chamber 14. The top of the rectangular tube chamber 14 is sealed. The the separation layer which has a funnel shape 15 with a round hole in the center is provided in the round tube chamber 13. The diameter of the hole is adapted to the diameter of the faeces sampling stick 8, so that the threaded structure 19 of the faeces sampling stick 8 passes to scrape residual faeces on the threaded surface.

The size and shape of the stop block 3 are adapted to the section of the rectangular tube chamber 14. The bulge 20 is provided on the inside wall and adapted to a small hole 18 of the lid 1, so as to realize dismounting and fixing of the stop block 3. The stop block 3 is located at the top of the rectangular tube chamber 14, so as to prevent the faeces sampling stick 8 from inserting in advance due to misoperation.

A test strip slot 9 is provided at one side of the test strip slot seat 5. The test strip slot 9 communicates with the base 7, so that glass fiber at the bottom of the test strip may contact with the solution. The other side of the test strip slot seat 5 is a piston slot 12 with a hole in the center. Two piston supports 10 are provided on the upper edge of the piston slot 12, so that the piston 4 is supported without sliding down before acting. The outer shape of the test strip slot seat 5 is adapted to the main body container sealed tube 2. The test strip slot 9 is inserted into the rectangular tube chamber 14. The piston slot 12 is located in the round tube chamber 13.

The base 7 is sleeved with the bottom of the test strip slot seat 5. A solution receiving slot 21 is provided in one side of the base 7. A groove 22 is located below the test strip slot 9 at the other side. A slope is provided between the receiving slot 21 and the groove 22. The quantitative solution entering the receiving slot 21 via the piston slot 12 is guided to flow into the groove 22 via the slope, so that the glass fiber at the bottom of the test strip just contacts with the solution in the groove 22. The mixed solution starts to spread under the siphon action of the glass fiber of the test strip, and then a color zone appears.

The sealing sheet 6 is clung to the back of the piston slot 12 to seal the small hole in the piston slot 12, and the piston 4 is placed on the piston supports 10. At the moment, no solution exists in the base 7, and after the piston 4 is pressed down, the piston rod 11 with a sharp end can pierce the sealing sheet 6, so that the solution enters the receiving slot 21 of the base 7 quantitatively.

The diameter of one end, close to the lid, of the faeces sampling stick 8 is greater than that of the free end (the end with the threaded structure), so as to be matched with the round hole inside the separation layer 15 more tightly.

The volume of the piston slot 12 is set according to a quantitative requirement.

The main body container sealed tube 2, the test strip slot seat 5 and the base 7 are assembled together, and hermetical welding of the three is achieved by adopting an ultrasonic welding technology.

The Mounting Sequence:

1. The bulge 20 of the stop block 3 is inserted into the small hole 18 of the lid, the faeces sampling stick 8 is inserted into the round tube chamber 13 of the main body container sealed tube 2 already filled with the stabilizing solution, at the moment, the stop block 3 is located at the top of the rectangular tube chamber 14, the inner ring of the lid and the opening of the round tube chamber of the main body container sealed tube 2 are tightly sealed, and the faeces sampling stick 8 and the round hole inside the separation layer 15 are sealed, so that the liquid does not leak during storage and transportation.

2. The piston is placed on the piston supports 10, and the sealing sheet 6 is stuck at the back of the piston slot 12, so as to seal the piston slot 12.

Figure 8:
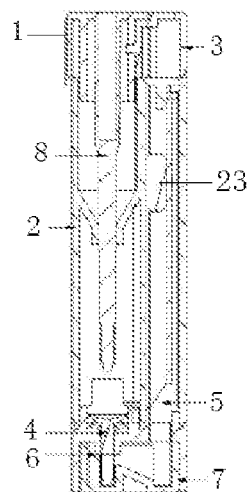
FIG. 8 is a state diagram before use of the device of the present invention.

3. The test strip is inserted into the test strip slot 9, the base 7 is combined with the test strip slot seat 5 and is sealed by ultrasonic welding, a drying agent 23 (referring to FIG. 8) is put into the clearance in the rectangular tube chamber 14, so as to play a role of protecting the humidity-sensitive colloidal gold test strip, and the lower side of the container sealed tube 2 is sleeved with the test strip slot seat 5, so as to form a sealed device.

Embodiment 2 Using Method of the Device

1. The lid 1 is taken down, and faeces is collected with the free end of the faeces sampling stick, so that the faeces stains the threaded part of the faeces sampling stick.

2. The faces sampling stick 8 is inserted back into the round tube chamber 13, and the utensil is shaken, so that the faeces is sufficiently dissolved in the solution.

3. The stop block 3 is dismounted, the lid 1 is pressed to the bottom, at the moment, the faeces sampling stick pushes down the piston 4, so that the sharp end of the piston rod 11 pierces the sealing sheet 6, and the quantitative mixed solution in the piston slot 12 enters the receiving slot 21 of the base 7.

4. The mixed solution is allowed to flow into the groove 22 of the base 7 via the slope, wherein the bottom of the groove 22 just contacts with the glass fiber at the bottom of the test strip, the mixed solution starts to spread under the siphon action of the test strip, and then a color zone appears.

5. After 10 minutes, the color of the quality control line of an observation window of the test strip and the color of a detection line strip are checked, comparison is conducted with a color card, and a result is determined.

Embodiment 3

Compared with the structure of the prior art, the present invention has the following advantages:

1. The product production efficiency is increased, and the operation procedure is reduced: ultrasonic welding is adopted for the base, only a few seconds is needed for welding one base, while previous products need to be smeared with glue, and 8 hours or more are needed for completely bonding the products.

2. The product quality is improved: ultrasonic welding ensures that the base is sealed, so as to reduce or completely eradicate the risk of liquid leakage. The previous products are smeared with glue, and the glue causes influence to the functions of the buffer solution and spreading of the test strip, and then product sensitivity is reduced or false positive is caused.

3. The use convenience is increased: the test is completed by just unplugging the lid, sampling, inserting the lid back, shaking, unplugging the stop block, pressing down the lid, and determining the color zone appearing by spreading in set time. For previous products, the test is completed by unplugging the lid, sampling, inserting the lid back, shaking, tearing down a safety paster, pressing down the lid, unplugging the lid to the home position, pinching the tube body by exerting strength, and waiting for the outer shape of the color zone. The time for the outer shape of the color zone is uncontrollable, the strength for different operators to pinch the tube body is uncontrollable, and then the determination result is great in difference.

4. The sample liquid needed for spreading can be quantified, and for each product, the volume of the liquid pushed to transfer by the piston is the same, without being affected by different operators. For the previous products, different persons pinch the tube body, and because the pinch strength is different, the transferred liquid amount is uncontrollable.

What is claimed is:

1. An integrated device for faeces sampling and occult blood detection, comprising a lid (1), a main body container sealed tube (2), a stop block (3), a piston (4), a test strip slot seat (5), a sealing sheet (6), a base (7), and a faeces sampling stick (8), the lid (1) being provided with an inner ring (16) and a C-shaped outer ring (17), the diameter of the inner ring (16) fitting the inner diameter of a round tube chamber (13), the diameter of the C-shaped outer ring (17) fitting the outer diameter of the round tube chamber (13), a clearance between the inner ring (16) and the C-shaped outer ring (17) fitting the size of a tube wall of the round tube chamber (13), the faeces sampling stick (8) being fixed at the center of the inner ring (16), a free end of the faeces sampling stick (8) being provided with a threaded structure (19), the faeces sampling stick (8) fitting a round hole inside a separation layer (15), a small hole (18) being provided in a tube wall of the inner ring (16) at an opening of the C-shaped outer ring (17) fitting a bulge (20) of the stop block (3), the main body container sealed tube (2) comprising the round tube chamber (13) for storing liquid and a rectangular tube chamber (14), the round tube chamber (13) comprising the separation layer (15) having a funnel shape and the round hole inside, the stop block (3) sitting on the top of the rectangular tube chamber (14), a test strip slot (9) being provided at one side of the test strip slot seat (5), a piston slot (12) with a hole in the center being provided at the other side of the test strip slot seat (5), two piston supports (10) being provided on an upper edge of the piston slot (12), the test strip slot seat (5) fitting inside the main body container sealed tube (2), the base (7) being sleeved with the bottom of the test strip slot seat (5), a solution receiving slot (21) being provided on one side of the base (7), the other side of the base (7) being provided with a groove (22) in a part located below the test strip slot (9), a slope being provided between the receiving slot (21) and the groove (22), and the sealing sheet (6) being clung to a back of the piston slot (12), and the piston (4) being placed in the piston supports (10).

2. The integrated device for faeces sampling and occult blood detection according to claim 1, wherein the round hole inside the separation layer (15) tightly fits the faeces sampling stick (8).

3. The integrated device for faeces sampling and occult blood detection according to claim 1, wherein the test strip slot (9) communicates with the base (7).

4. The integrated device for faeces sampling and occult blood detection according to claim 1, wherein a volume of the piston slot (12) is set according to a quantitative requirement.

5. The integrated device for faeces sampling and occult blood detection according to claim 1, wherein the test strip slot (9) is inserted into the rectangular tube chamber (14), and the piston slot (12) is located in the round tube chamber (13).

6. The integrated device for faeces sampling and occult blood detection according to claim 1, wherein the diameter of an end, close to the lid, of the faeces sampling stick (8) is larger than that of the free end of the faeces sampling stick (8), and the faeces sampling stick (8) tightly fits the round hole inside the separation layer (15).

7. The integrated device for faeces sampling and occult blood detection according to claim 1, wherein the main body container sealed tube (2), the test strip slot seat (5) and the base (7) are hermetically welded and assembled together by using an ultrasonic welding technology.

\* \* \* \* \*